United States Patent
Walker et al.

(10) Patent No.: US 6,679,250 B2
(45) Date of Patent: Jan. 20, 2004

(54) COMBINATION INHALATION THERAPEUTIC AND EXHALATION MEASURING DEVICE

(76) Inventors: Joseph J. Walker, 3230 Coral Lake La., Coral Springs, FL (US) 33065; Frank A. Schimansky, III, 10701 NW. 43$^{rd}$ Ct., Coral Springs, FL (US) 33065

(*) Notice: Subject to any disclaimer, the term of this patent is extended or adjusted under 35 U.S.C. 154(b) by 133 days.

(21) Appl. No.: 10/091,648

(22) Filed: Mar. 6, 2002

(65) Prior Publication Data

US 2003/0168058 A1 Sep. 11, 2003

(51) Int. Cl.$^7$ .............................................. A61M 11/00
(52) U.S. Cl. ........................ 128/200.21; 128/200.14; 128/200.18; 128/200.24; 128/203.12; 128/204.14; 600/538
(58) Field of Search .................. 128/200.14, 200.18, 128/200.21, 200.22, 200.24, 203.12, 203.15, 203.25, 204.14; 600/538, 540

(56) References Cited

U.S. PATENT DOCUMENTS

| | | | | |
|---|---|---|---|---|
| 757,013 A | * | 4/1904 | Bennett ................. 128/203.25 |
| 4,198,969 A | * | 4/1980 | Virag ..................... 128/200.21 |
| 4,210,155 A | * | 7/1980 | Grimes ........................ 600/540 |
| 4,253,468 A | * | 3/1981 | Lehmbeck .................. 600/539 |
| 4,259,951 A | * | 4/1981 | Chernack et al. ...... 128/200.14 |
| 4,268,460 A | * | 5/1981 | Boiarski et al. ................ 261/1 |
| 4,944,306 A | * | 7/1990 | Alvino ........................ 600/538 |
| 5,040,527 A | * | 8/1991 | Larson et al. .......... 128/200.23 |
| 5,165,392 A | * | 11/1992 | Small, Jr. ............... 128/200.18 |
| 5,415,161 A | * | 5/1995 | Ryder ..................... 128/200.23 |
| 5,427,089 A | * | 6/1995 | Kraemer ................ 128/200.23 |
| 5,431,154 A | * | 7/1995 | Seigel et al. ........... 128/200.14 |
| 5,522,380 A | * | 6/1996 | Dwork ................... 128/200.23 |
| 5,617,844 A | * | 4/1997 | King ...................... 128/200.18 |
| 5,839,430 A | * | 11/1998 | Cama ..................... 128/200.14 |
| 6,412,481 B1 | * | 7/2002 | Bienvenu et al. ...... 128/200.21 |
| 6,539,939 B2 | * | 4/2003 | Rubin .................... 128/203.15 |

* cited by examiner

Primary Examiner—Weilun Lo
Assistant Examiner—Joseph F. Weiss, Jr.
(74) Attorney, Agent, or Firm—Kenneth E. Merklen

(57) ABSTRACT

A combination spirometer or peak flow meter and nebulizer system is provided. Utilization of common elements, on a time sharing basis is accomplished by the combined instrumentation. The sharing of a common chamber by a peak flow meter and a nebulizer system is controlled by valves operated in response to phases of the respiratory process of a patient. With this combination vaporized medication is provided to a patient for inhalation during the inhale phase of the respiration cycle and the effectiveness of the inhaled medication is monitored by measuring the rate of flow of the breath exhaled during the exhale phase of the same respiratory cycle.

11 Claims, 2 Drawing Sheets

Figure 2:
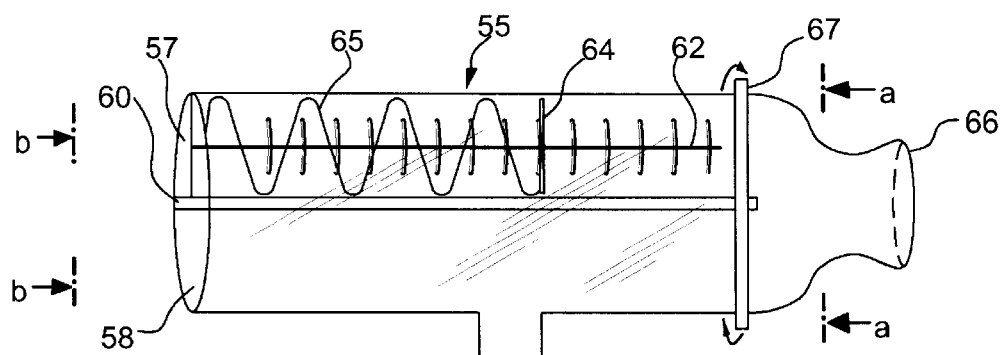

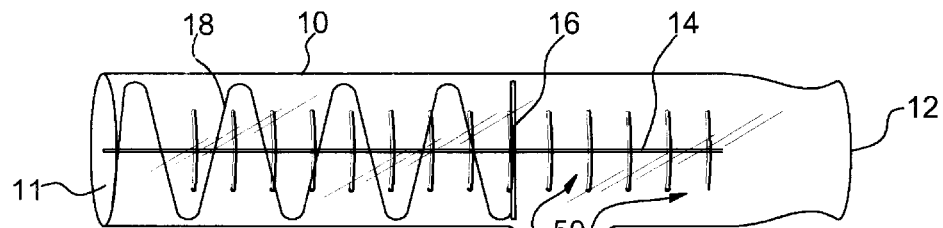
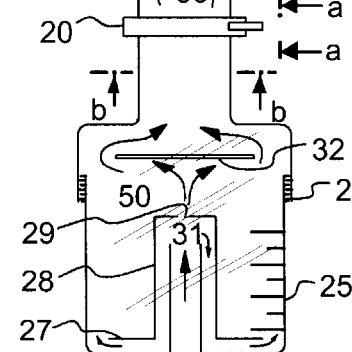
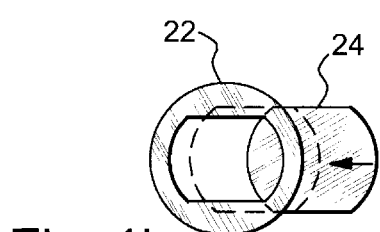
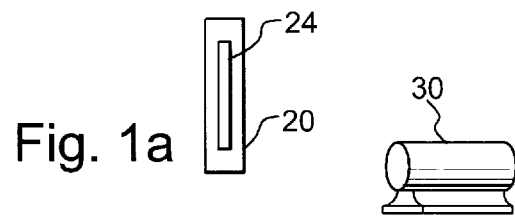
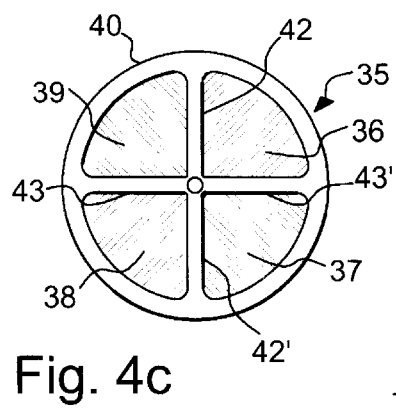
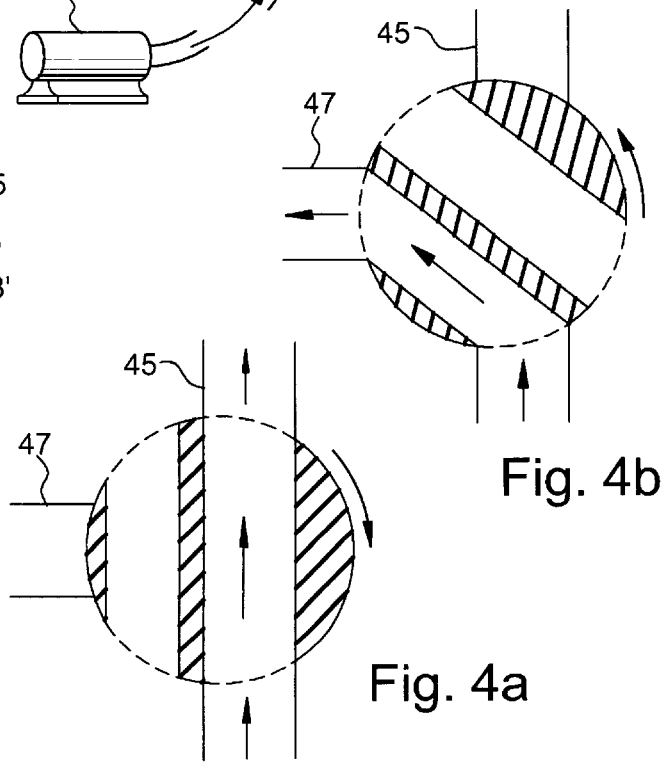

COMBINATION INHALATION THERAPEUTIC AND EXHALATION MEASURING DEVICE

BACKGROUND OF THE INVENTION

1. Field of the Invention

The present invention relates to the field of respiratory therapy. In particular, the invention is a unique medical instrumentation combining a meter for measuring the peak ability for exhalation of a patient with the administration of inhalation therapy for the patient.

2. Prior Art

Peak flow meters for measuring the maximum rate at which air is forced from the lungs during exhalation are used by inhalation and respiratory therapists and physicians for monitoring a patient's respiratory condition for diagnosing potential and/or existing breathing problems. The meter generally comprises an open ended cylinder, marked with a graduated scale along its length. The patient breaths into the open ended cylinder, through a mouth piece, the patient's breath impinging against a biased diaphragm. The biased diaphragm is moved down the cylinder, along the scale thus indicating a rate at which breath is exhaled from the lungs. A nebulizer is a device often used by inhalation and respiratory therapists and physicians for administering vaporized medication to a patient, presenting vaporized medication to a patient through an aerosol chamber or vapor holding cylinder. Through a mouth piece, at an end of the vapor holding cylinder, a patient inhales vaporized medication. Peak flow meters and nebulizers are each well known and often used medical instrumentations. The U.S. Pat. No. 4,944,306, issued to Alvino, Jul. 31, 1990 teaches an improved, patient adjustable, viewable, exhalation flow rate metering device or spirometer, also called a peak flow meter. A vertical housing, open at its upper end, connects, at its lower end to an horizontal cylinder with a mouth piece at one end and an open end at the other end. The connection between the vertical housing and the cylinder is at a point between the mouth piece and the open end of the cylinder. The vertical housing supports a biased piston on a positioning rod. The biased piston is in full view of the patient exhaling into the mouth piece and cylinder. Exhaled breath from the patient forces the biased piston up the positioning rod. The patient watches the piston rise up the positioning rod as the patient blows into the mouth piece. U.S. Pat. No. 5,565,630, issued to Shene, Oct. 15, 1996 teaches an improved peak flow meter for measuring peak exhalation air flow of a patient. Breath is exhaled, from the mouth, through a mouth piece, into a hollow chamber containing a biased, movable member which moves along the hollow chamber in response to pressure. A series of vent holes are provided in the wall of the chamber, along the path of the biased member. The holes increase in diameter as the length of the path increases. A graduated scale is marked on the cylinder, along the path. The biased, movable member moves along the path and graduated scale in response to pressure of a person's or patient's breath exhaled into the mouth piece. The position of the biased, movable member, along the graduated scale, indicates a peak breath flow of a person's exhalation.

Nebulizers which meter vaporized medication to a person, are well known in the medical field. Examples of United States issued patents are:

| | |
|---|---|
| #3,353,536 issued to F.M. Bird et al | Nov. 21, 1967 |
| #4,470,412 issued to Nowacki et al | Sept. 11, 1984 |
| #5,040,527 issued to Larson et al | Aug. 20, 1991 |
| #5,363,842 issued to Mishelevich et al | Nov. 15, 1994 |
| #5,415,161 issued to Ryder | May 16, 1995 |
| #5,431,154 issued to Seigel et al | Jul. 11, 1995 |
| #5,743,252 issued to Rubsamen et al | Apr. 28, 1998 |

The U.S. patent to F. M. Bird et al, U.S. Pat. No. 3,353,536 teaches a nebulizer which is essentially a fixed or stable unit and can be used for long term use. A relatively large container supports a large amount of liquid medication. Air, flowed into a large quantity of liquid medication, vaporizing the liquid which, in vapor form is presented to the patient for inhalation. The unit is designed for long term therapy where oxygen or air is administered to a patient. The U.S. Pat. No. 4,470,412, issued to Nowacki et al, teaches an inhalation valve for an antiasthmatic medication cartridge assembly. A pressurized cannister or cartridge containing a suitable medication for inhalation is used for dispensing high velocity bursts of a pressurized medicated inhalant, in vaporized form, into a sealed chamber. One end of the chamber is sealed by a slit diaphragm valve with an open mouth piece on the output side of the split valve. The valve opens when the patient inhales, passing the vaporized medication to the patient for inhalation. The dosage of vaporized medication is user controlled. The slit valve fails to retain bursts of vaporized medication from the cannister containing pressurized medication.

The U.S. Pat. No. 5,040,527, issued to Larson et al; U.S. Pat. No. 5,363,842, issued to Mishelevich et al; U.S. Pat. No. 5,415,161, issued to Ryder; and U.S. Pat. No. 5,743,252, issued to Rubsamen et al each teach the use of a replaceable cannister containing a pressurized aerosol inhalant, a vaporized medication, under high pressure. Upon release from the cannister, an high velocity burst of vaporized medication is entrapped in and fills a patient breathing cylinder and mouth piece through which the patient is breathing. The high velocity burst of medication from the pressurized cannister results in an excess portion of the drug being administered to the patient and depositing the excess portion in the patient's mouth. The high velocity burst of medication from the pressurized cannister also results in a loss of medication through the openings in the breathing cylinder. U.S. Pat. No. 5,431,154, issued to Seigel et al also teaches the use of a replaceable, aerosol cannister of vaporized medication under pressure and further teaches limiting the pressure of the burst of high velocity spray of medication after the burst is released from the cannister.

The U.S. Pat. No. 5,522,380, issued to Dwork and U.S. Pat. No. 5,839,430, issued to Cama each teach a combination peak flow meter and metered dose inhaler. However, each patent teaches the use of a pressurized cannister which contains vaporized medication under high pressure. In the case of Cama, the complete cannister of pressurized medication is inserted into the breathing chamber of the device so that bursts of medication are emitted from the cannister directly into the mouth piece of the device and therefore into the mouth of the patient. In the case of Dwork, in the output nozzle of the high pressure cannister is inserted directly into the breathing chamber of the device. In each case, the high velocity burst of medication into the breathing chamber deposits an huge amount of medication into the mouth of the patient and medication is lost out the vent hole in the breathing chamber. Dosage from the cannister, in bursts of high velocity medication, is patient controlled. By depositing high velocity bursts of medication directly into the chamber or cylinder of the peak flow meter, medication is lost up the calibrated cylinder of the peak flow meter and inaccuracy in the peak flow meter is amplified by getting the movable diaphragm, in the case of Cama, and a ball float in the case of Dwork, wet from the vaporized medications burst into the unit.

SUMMARY OF THE INVENTION

The present invention provides a peak flow meter and nebulizer, combined to provide patients and clinicians with an improved medical device which delivers vaporized medication to a patient, for inhalation, and monitors the patient's air intake during the same respiratory cycle. Peak flow rate meters may be used to determine the severity of air flow obstruction caused by the swelling of tissue in the respiratory system. Monitoring the peak flow rate directly after medication for relief of air flow obstruction has been taken, can determine the immediate effectiveness of the medication.

A peak flow meter consists of an open ended chamber for capturing exhaled breath, in an expandable space, for measuring the flow rate of breath expelled from a patient. The exhaled breath-capturing chamber or breathalizer chamber is an open ended chamber, with a mouth piece at the other end. The chamber houses a lightly biased, movable baffle or diaphragm which moves within the chamber in accordance with the flow rate of breath exhaled into the chamber. A graduated scale, marked along the cylinder is used for measuring the breath exhaled into the cylinder. The nebulizer is a medication delivery device or system which delivers medication, in vaporized or mist form, for inhalation by a patient. The nebulizer includes a vapor or mist capturing chamber or breathalizer chamber, which is open at one end, with a mouth piece at the other end. The vaporized medication capturing chamber or breathalizer chamber permits the patient to inhale, unobstructedly, the vaporized medication delivered to the breathalizer chamber, along with air.

From one aspect of the invention, there is provided a peak flow meter and a nebulizer, connected so as to use a common breathalizer chamber. The peak flow meter comprises an opened cylinder with a mouth piece at the other end. A lightly biased baffle or diaphragm is supported in the breathalizer chamber for capturing exhaled breath and defining a space in the breathalizer chamber, which is a function of the flow rate of the breath exhaled from a patient through the mouth piece. The nebulizer is a vapor or mist generating and delivery device or system which converts a liquid medication, for example, into a mist or vaporized medication by bubbling air or oxygen, under low pressure, through the liquid medication. The vaporized medication is delivered to a patient for inhalation, along with air or oxygen. In accordance with the present invention, vaporized medication of a nebulizer is delivered to the common breathalizer chamber, for inhalation, with air or oxygen. A one way valve is provided between the common breathalizer chamber and the vaporization unit of the nebulizer. Connection by the medication vaporization unit of the nebulizer to the breathalizer chamber is at a point between the normal position of the lightly biased diaphragm and the mouth piece at the end of the breathalizer chamber. A one way valve between the vaporization unit and the common chamber maintains the integrity of the measurement of the peak flow meter and permits delivery of the vaporized medication. The one way valve may be an automatic leaf valve or ball check valve or may be a manually operated, spring loaded sliding plate valve or a rotatable ball channel valve.

From another aspect of the invention, a peak flow meter and a nebulizer are combined with individual corresponding units in parallel relationship where the corresponding units have common ends and a valve for connecting a common mouth piece to the respective corresponding units. A single cylinder or elongated chamber, with a mouth piece at one end and an open end at the other end, is divided into two, essentially parallel chambers by a common wall. One chamber serves as a breathalizer chamber for the peak flow meter and the other chamber serves as a breathalizer chamber for the nebulizer system. The common mouth piece at one end of the single cylinder includes a valve that shuts off one breathalizer chamber from the common mouth piece and opens the other breathalizer chamber to the common mouth piece. The valve may be a manually operable valve, such as a rotatable half open disk valve or an automatic valve such as a double leaf one way valve, with one leaf of the double leaf valve opening in response to exhalation through the mouth piece and closing in response to inhalation through the mouth piece while the second leaf of the double leaf valve closes in response to exhalation through the mouth piece and opens in response to inhalation through the mouth piece.

From a further aspect the invention provides a spirometer or peak flow meter combined with a nebulizer which share common components. Each device utilizes common components individually, to the exclusion of the other, on a time share basis. The time shared is the time of the respiratory cycle of a patient.

BRIEF DESCRIPTION OF THE DRAWINGS

FIG. 1 is a representation of a preferred embodiment of the invention, in pictorial view;

FIG. 1*a* is a representation of a view along line a—a in FIG. 1;

FIG. 1*b* is a representation of a view along line b—b in FIG. 1;

FIG. 2 is a representation of an alternate embodiment of the invention, in pictorial view;

FIG. 2*a* is a representation of a view along lines a—a in FIG. 2 showing a rotatable disk valve;

FIG. 2*a'* is a representation of a view along lines a—a in FIG. 2 showing a dual leaf valve, with the leafs operable in opposite directions, respectively;

FIG. 2*b* is a representation of a view along lines b—b in FIG. 2:

FIG. 3 is a representation of a rotatable mouth piece half-block valve usable in the invention;

FIGS. 4*a* and 4*b* are representations of a ball channel valve in different positions, the ball channel valve usable in the invention;

FIG. 4*c* is a representation of a four leaf split one way valve usable in the invention; and FIG. 4*d* is a representation of a ball check valve, usable in the invention.

DETAILED DESCRIPTION OF THE INVENTION

FIG. 1 represents a preferred embodiment of the invention where a common chamber for the collection and measurement of the rate of flow of exhaled breath and for the deposition of a vaporized medication for inhalation is provided. A cylinder or chamber 10 is open ended at 11 and has a mouth piece 12, at the other end. Within the cylinder is a guide wire member 14 for a displaceable diaphragm or baffle 16. The diaphragm 16 is lightly biased by a hair spring 18, so as to return to its normal position, in absence of breath exhaled into the mouth piece.

The cylinder or breathalizer chamber 10 is preferably fabricated from a clear material, such as plastic, for example so that one may easily view the diaphragm 16, on the inside of the cylinder. A graduated scale is marked on the wall of the cylinder so that the location of the diaphragm can be noted. The diaphragm is positioned a few marks beyond the beginning of the scale to account for the bias, which is very light but sufficient to return the diaphragm to its normal position.

Figure 4D:
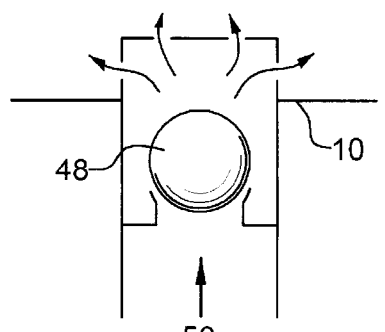

The vaporization unit of the nebulizer system is connected to the breathalizer chamber 10 at a point between the mouth piece 12 and the at rest position of the diaphragm 16. A one way valve 20 closes off the vaporization unit of the nebulizer from the breathalizer chamber 10, during periods of exhalation by the patient. The valve 20 is represented in its open condition in FIGS. 1a and 1b. The valve 20 is represented as a spring loaded, push disk valve, for convenience, although an one way split leaf, automatic valve is preferred. The valve 20 includes an open center housing 22 which supports a spring or bias means, not shown, and a disk or plate 24. The biased push valve is represented mostly closed, in broken line form in FIG. 1b. The vaporization unit of the nebulizer includes a container 25 with that is thread-connected to the cap 26. The output of cap 26 is connected to the input side of the valve 20. A ported distribution cap 28, with a top port 29 sits off the bottom of the container 25 so that when gas 31, such as air or oxygen, for example, from the pump 30, is blown into the ported cap 28 of the container 25, the gas will be distributed out the top port 29 of the ported cap 28 and out, under the flanged base 27. When a liquid is in the container 25, the gas 31 pumped into the container by the pump 30, is driven into the ported distribution cap 28, out of the top and bottom of the cap and into the liquid, mixing with the liquid, forming a mist or vapor of the liquid and gas. This instrumentation is used for vaporizing liquid medication placed in the container 25, and administrating the vaporize liquid medication to a patient, by inhalation. A baffle 32 blocks direct access of the vaporized mass to the valve 20 and hence to the breathalizer chamber 10. With the valve 20 open, the vaporized mass is flowed gently into the breathalizer chamber for inhalation by a patient through the mouth piece 12. FIG. 4c represents an automatic valve 35 that may be substituted for the valve 20, represented in FIG. 1b, in an alternative embodiment. The valve 35 is a four leaf, one way valve. Each of the four leafs 36, 37, 38 and 39 are connected to the rim of the housing 40 and each of the leafs lay on the same side of the radial bars 42, 42' 43 and 43'. FIGS. 4a and 4b represent another alternate valve, a channeled ball valve, that may be substituted for the biased disk valve at 20. FIG. 4a represents a valve position, with the main channel 45 open and the minor or vent channel 47 closed. FIG. 4b represents a valve position, with the main channel 45 closed and the vent channel 47 open. The channeled ball valve is a manual operated valve and is manually rotated to change position of the channels. FIG. 4d represents another automatic valve that may be used at the position of valve 20. FIG. 4d represents a ball check valve. The ball 48 sits in the valve seat, the weight of the ball holding against the low pressure of the vaporized mass 50 in the container 25. Upon inhalation through the mouth piece 12, the ball is unseated, opening the valve, permitting the vaporized medication to pass through the valve and enter the breathalizer chamber. Upon exhalation, the ball is seated in the valve seat, closing the valve, maintaining the integrity of the peak flow measurement.

FIG. 2 represents an alternate embodiment of the invention. The peak flow meter and nebulizer system share a common mouth piece and have separate breathalizer chambers, each of which have a common wall and common ends open. The alternate embodiment of the invention comprises a cylinder 55 separated into two chambers, 57 and 58 by a divider wall 60. The breathalizer chamber 57 supports a guide means 62 on which a baffle or diaphragm 64 rides. The diaphragm 64 is biased by an hair spring 65, which returns the diaphragm 64 to its at rest position in the breathalizer chamber 57. A mouth piece 66 is connected to the cylinder 55 at one end, with a valve 67 at the internal end of the mouth piece. The valve 67 may be similar to the valve 67a represented in FIG. 2a. The valve represented is a manually rotatable, disk valve, half of which is open 63 and half of which is closed 61. The valve may be rotated for opening one chamber, for example 58, to the mouth piece 66 and closing the other chamber 57, to the mouth piece 66, then rotated to a reverse condition.

Figure 2A:
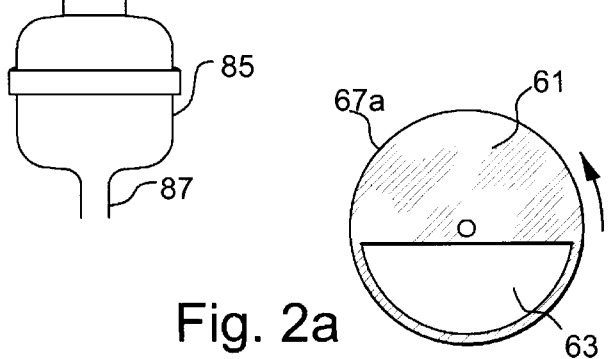
Figure 2B:
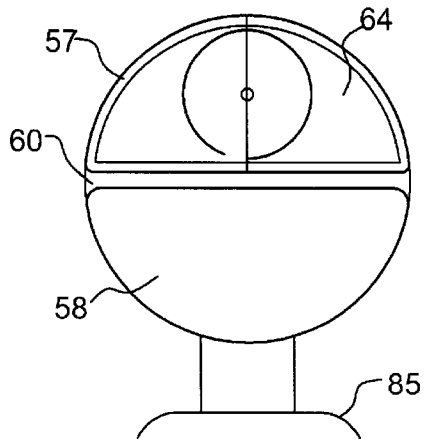
Figure 2A:
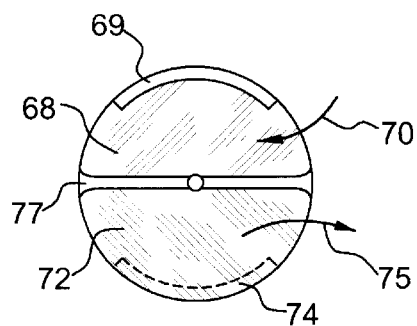

Alternatively, the valve represented in FIG. 2a' may be used. The valve represented in FIG. 2a' is an automatic two way double leaf valve. One leaf 68 is secured to an arcuate section 69 on the ring housing 71 and opens, for example, outwardly, as indicated by arrow 70. The other leaf 72 is secured at an arcuate section 74 on the ring housing 71 and opens, for example, inwardly, as indicated by the arrow 75. The free ends of each leaf rest on opposite sides, respectively of the diameter bar 77. When operating, one leaf is open and the other leaf is closed.

Figure 3:
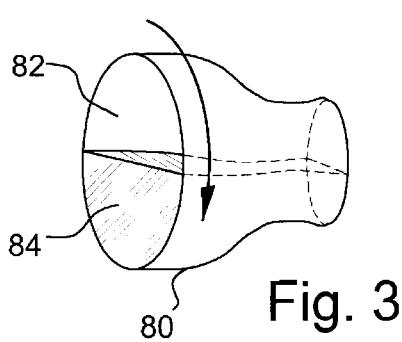

As an alternative to the valve at 67, the mouth piece 66 may be used as a valve. As shown in FIG. 3 the mouth piece 80 includes an open section 82 and a closed section 84. The open section 82 may be aligned with the chamber 57, thus closing chamber 58 by the closed or blocking section 84. The mouth piece may be rotated to reverse the condition. The nebulizer system of the embodiment in FIG. 2 includes the breathalizer chamber 58 and vaporizer 85. The vaporizer 85 may be similar to the vaporizer represented in FIG. 1, with a pump pumping air or oxygen through the tubing 87. With an automatic two way valve at 67, for example, the alternate embodiment of the invention may be used to administer inhalation medication during the inhale stage of the respiration process and the peak flow of the patient may be measured during the exhale stage of the respiration process.

In the foregoing description of the invention, referenced to the drawings, certain terms have been used for conciseness, clarity and comprehension. However, no unnecessary limitations are to be implied from or because of the terms used, beyond the requirements of the prior art, because such terms are used for descriptive purposes and are intended to be broadly construed. Furthermore, the description and illustration of the invention are by way of example, and the scope of the invention is not limited to the exact details shown, represented or described.

Having now described a preferred embodiment of the invention, in terms of features, discoveries and principles, along with certain alternative construction and suggested changes, other changes that may become apparent to those skilled in the art may be made, without departing from the scope of the invention defined in the appended claims.

What is claimed is:

1. A clinical respiration therapy device comprising:

a) a chamber means defined by a cylindrical body having an open end at one end and a mouth piece means at the other end, said cylindrical body having a graduated scale marked along said cylindrical body, said graduated scale marking a volume of space of said chamber from a minor volume space to a major volume space, said minor volume space defined by an indicator means spaced from said mouth piece means;

b) a guide means extending along said chamber means from said mouth piece means to said open end and supporting said indicator means, said indicator means for being displaced along said guide means from a position indicating said minor volume space in response to the flow rate of breath exhaled into said chamber means through said mouth piece means;

c) an input port means in said cylindrical body opening into said minor volume space;

d) a one way valve means across said input port means for preventing breath exhaled into said chamber means from escaping said chamber means through said input port means;

e) a container means having an input means and an output means, said container means adapted for holding a liquid within said container means, said input means for receiving a gas under pressure for mixing with said liquid in said container means for generating a vaporized mass; and f) said output means coupled to said one way valve means for depositing said vaporized mass into said chamber in said minor volume space.

2. A clinical respiration therapy device as in claim 1, and further including a pump means for pumping said gas into said container means at a low pressure.

3. A clinical respiration therapy device as in claim 2, wherein said gas is air and said liquid is a medication preparation.

4. A clinical respiration therapy device as in claim 2, wherein said gas is oxygen and said liquid is a medication preparation.

5. A clinical respiration therapy device as in claim 1 wherein said one way valve means is a leaf valve biased to hold said vaporized mass in said container means and said leaf valve opens upon inhalation through said mouth piece means.

6. A clinical respiration therapy device as in claim 1 wherein said one way valve means is a biased disk push valve.

7. A clinical respiration therapy device comprising:

a) a cylindrical body having an open end at one end and a mouth piece means at another end and a common wall means for separating said cylindrical body into a first chamber and a second chamber, said common wall means extending from said open end to said mouth piece means;

b) a guide means extending along said first chamber and supporting an indicator means, said indicator means for being displaced along said guide means from a position indicating a minor volume space in said first chamber to another position, toward a major volume space in said first chamber, in response to breath exhaled into said first chamber through said mouth piece means;

c) a port means in said cylindrical body providing a first input means into said second chamber;

d) a valve means between said mouth piece means and said cylindrical body, said valve means having a first condition and a second condition, said first condition for closing access for said mouth piece means to said second chamber and opening access for said mouth piece means to said first chamber, said second condition for opening access for said mouth piece means to said second chamber and closing access for said mouth piece means to said first chamber;

e) a container means having a second input means and an output means, said container adapted for holding a liquid, said second input means for receiving a gas under pressure and for mixing said gas with said liquid for generating a vaporized mass; and f) said output means coupled to said first input means for delivering said vaporized mass into said second chamber.

8. A clinical respiration therapy device as in claim 2 wherein said first chamber includes a graduated scale marked along an uncommon wall of said first chamber defining volume of space in said first chamber.

9. A clinical respiration therapy device as in claim 3 wherein said indicator means is driven along said guide means by a breath exhaled through said mouth piece means and said indicator means indicates a space in said first chamber corresponding to a rate of flow of said breath.

10. A clinical respiration therapy device as in claim 2, wherein said valve means is an automatic, bidirectional, split leaf valve.

11. A clinical respiration therapy device as in claim 2, wherein said valve means is a rotatable disk valve, with half of said rotatable disk open.

* * * * *